United States Patent [19]

Bailly

[11] Patent Number: 5,380,311

[45] Date of Patent: Jan. 10, 1995

[54] APPLICATOR FOR EXTERNAL URINARY COLLECTION CATHETER, AND URINARY COLLECTION DEVICE COMPRISING SAID APPLICATOR

[75] Inventor: Pierre Bailly, Montrouge, France

[73] Assignee: Synthelabo, Le Plessis, France

[21] Appl. No.: 92,889

[22] Filed: Jul. 19, 1993

[30] Foreign Application Priority Data

Jul. 20, 1992 [FR] France .................. 92 08927

[51] Int. Cl.6 .............................................. A61F 5/44
[52] U.S. Cl. .................................................. 604/349
[58] Field of Search ........................... 604/349–353; 128/830, 842, 843, 844

[56] References Cited

U.S. PATENT DOCUMENTS

| 4,484,918 | 11/1984 | Omley ............... | 604/349 |
| 4,589,874 | 5/1986 | Riedel et al. ....... | 604/349 |
| 4,834,115 | 5/1989 | Stewart .............. | 128/842 |
| 5,211,640 | 5/1993 | Wendler ............. | 604/349 |

FOREIGN PATENT DOCUMENTS 284224 4/1988 European Pat. Off. .
WO88/02624 9/1988 WIPO .

Primary Examiner—Randall L. Green
Assistant Examiner—Rob Clarke
Attorney, Agent, or Firm—Fisher, Christen & Sabol

[57] ABSTRACT

A male urinary collection catheter kit which includes a catheter which has a flexible sheath which is placed in a leaktight manner onto a penis and which is rolled up prior to being placed on the penis, a tubular-shaped part which receives the glans of the penis and which is connected to the sheath and a tube in which urine is removed and which is connected to the sheath. There is also an applicator which has a ring, the diameter of which may be varied so that it can be slipped over the tubular-shaped part, then the diameter can be reduced until the ring is caught behind the glans, then the diameter can be maintained while the virga of the penis is pulled upon to cause it to extend so that the flexible sheath can be unrolled over the penis and then the diameter can be spontaneously increased so that the applicator can be removed from the catheter.

6 Claims, 5 Drawing Sheets

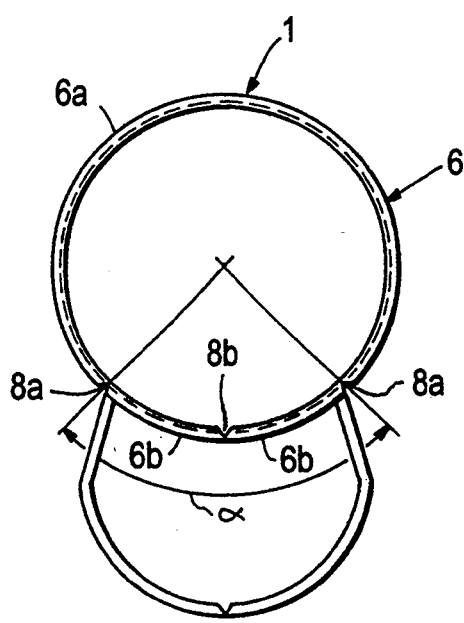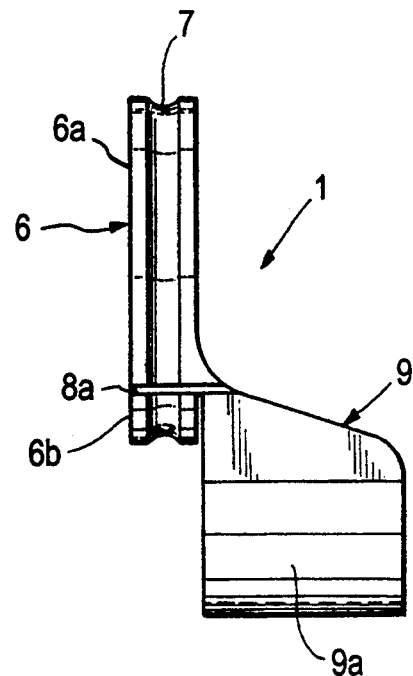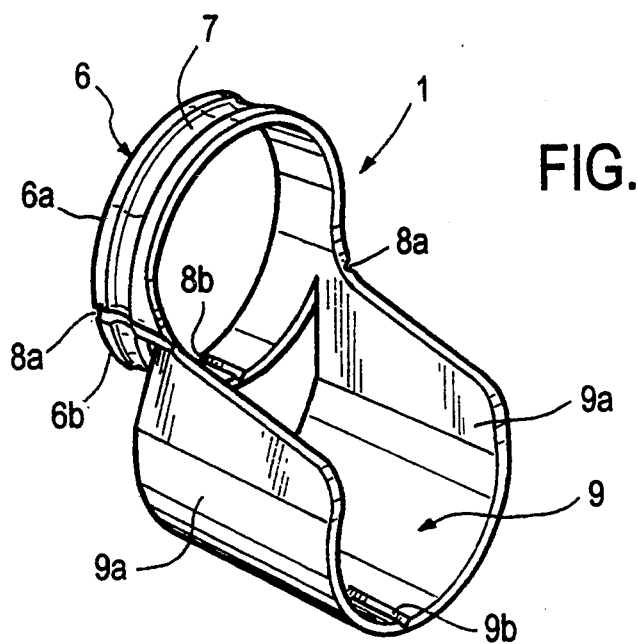
FIG. 9
FIG. 10
FIG. 8

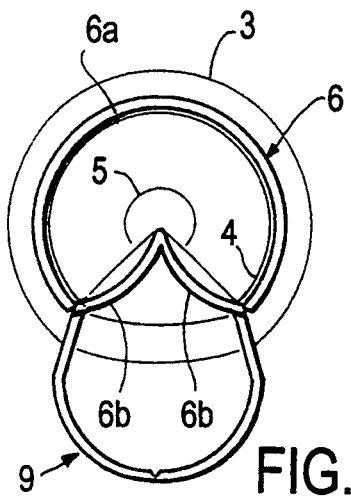
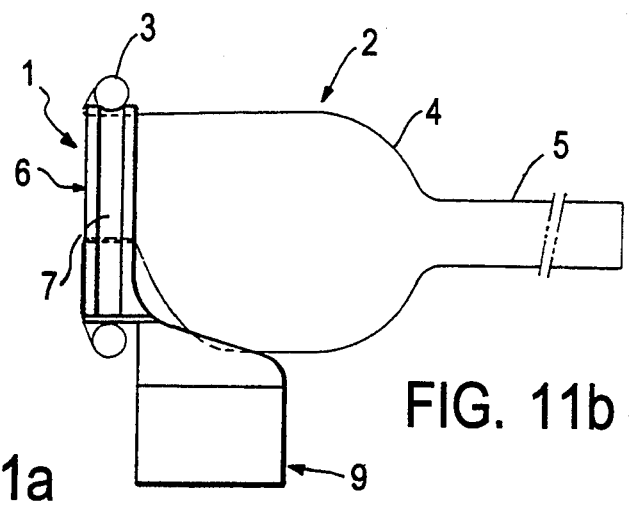
FIG. 11a
FIG. 11b
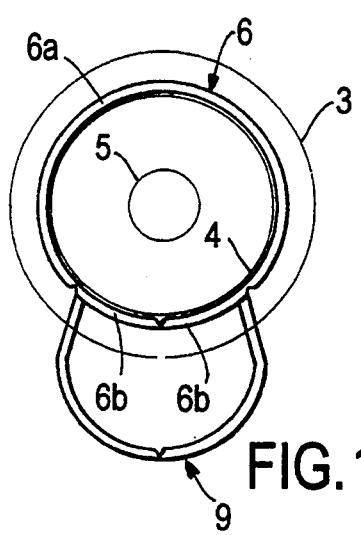
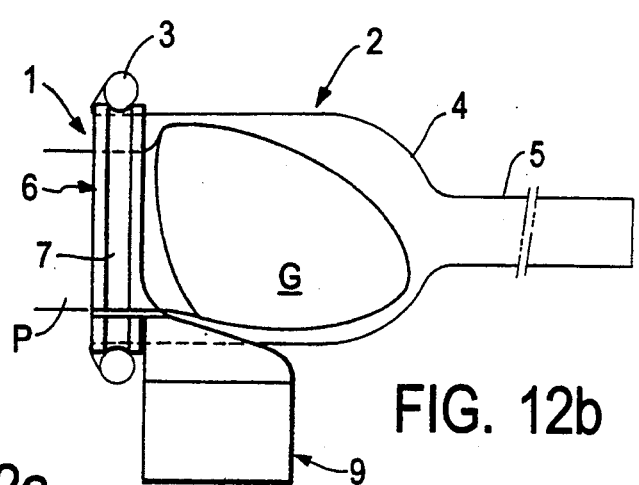
FIG. 12a
FIG. 12b
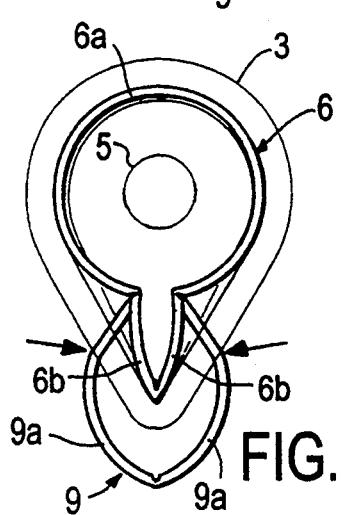
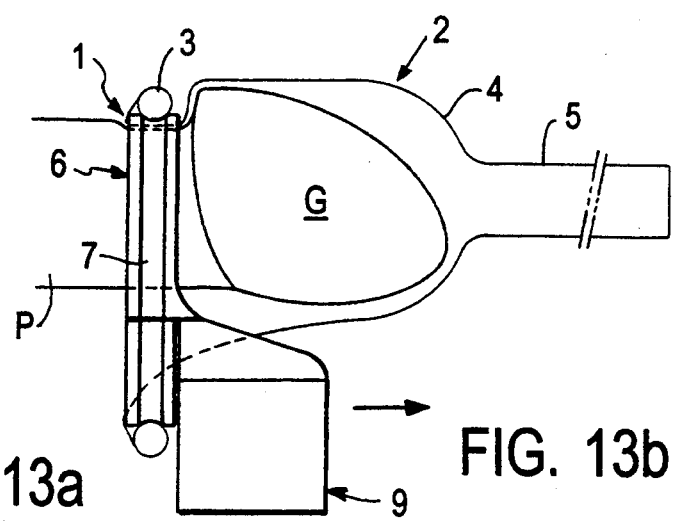
FIG. 13a
FIG. 13b

APPLICATOR FOR EXTERNAL URINARY COLLECTION CATHETER, AND URINARY COLLECTION DEVICE COMPRISING SAID APPLICATOR

The present invention relates to an applicator for an external urinary collection catheter for male individuals, and to a urinary collection device comprising said applicator.

Urinary collection devices are known which essentially comprise an external catheter comprising a flexible sheath intended to be applied in a leaktight manner onto the penis of a patient, which sheath is connected to a part for receiving the glans, substantially in the form of a spherical cap, itself connected to a tube for removing urine, said sheath being rolled up prior to its application. One difficulty consists in fitting such a catheter because of the lack of rigidity of the penis generally exhibited by the patient at the moment of application of the catheter. In order to fit the latter, it is therefore necessary to use an applicator. A catheter/applicator assembly is described, in particular, in U.S. Pat. No. 4,589,874. In this case, the applicator consists of a tubular body intended partially to surround the part for receiving the glans, and has an enlargement behind which the sheath is held in the rolled-up position, making it possible to avoid involuntary unrolling of said sheath. Furthermore, the body has recesses, which, during fitting of the catheter, act as openings for the fingers of the operator to grip the part for receiving the glans, and the end of the latter, while, with the other hand, the operator unrolls the sheath. However, under these circumstances, a retraction of the penis is often observed, so that it prevents fitting of such a catheter, despite the use of an applicator, in particular like the one described in U.S. Pat. No. 4,589,874.

The object of the present invention is to avoid this drawback, and relates to an applicator for an external primary collection catheter which is adapted in order to hold, in a positive manner, the penis, and to prevent it retracting during fitting of the catheter.

For this purpose, the applicator for an external urinary collection catheter, said catheter comprising a flexible sheath intended to be applied in a leaktight manner onto the penis of a patient, which sheath is connected to a part, for receiving the glans, of tubular shape, itself connected to a tube for removing urine, said sheath being rolled up prior to its application, is noteworthy, according to the invention, in that said applicator comprises a ring of variable diameter, having an initial diameter such that it can be slipped over said part for receiving the glans, said initial diameter being capable of being reduced, in a controlled manner, such that said ring can be caught behind the glans and hold the latter during the unrolling of the flexible sheath over the penis, and said ring being capable of resuming its initial diameter spontaneously, so that the said applicator can be removed from the said catheter.

Thus, by grasping the ring so as to make it catch behind the glans, the operator may pull on the virga so as to cause it to extend, in order thereby to facilitate the unrolling of the sheath onto it.

Advantageously, said ring comprises a peripheral part, extending over most of the circumference of the ring, and two adjacent peripheral segments, each delimited by folding lines of lesser thickness, such that, by pressing the two said segments towards each other, the ring is reduced to a ring substantially defined by said peripheral part.

Preferably, the two said segments extend over 120° symmetrically with respect to their common folding line.

In order to facilitate the gripping of the applicator by the operator, and to allow easy reduction of the diameter of the ring, the said two segments may be formed in a single piece with a trough-shaped gripping part, extending transversely to said ring in the extension of the two said segments, and itself separated into two portions by the extension of the folding line common to the two said segments.

However, according to one embodiment, the applicator may comprise a trough-shaped gripping part, extending transversely to said ring, separated into two portions by a central folding line, and integral, at its ends, with said ring, in the vicinity of the folding lines joining the two said segments to said peripheral part. This allows the sheath to be kept rolled up on the said ring, before application, in an unstretched manner, by pushing the two segments towards the inside of the ring, and thus the sheath, once unwound, to be prevented from forming folds.

Advantageously, the said ring comprises a peripheral groove for receiving said sheath in the rolled-up position.

The figures of the attached drawing will clearly show how the invention may be embodied. In these figures, identical references denote similar elements.

FIG. 8 is a perspective view of a second embodiment of an applicator for an external urinary collection catheter according to the invention.

FIG. 9 is a front view of the catheter in FIG. 8.

FIG. 10 is aside view of the catheter shown in FIG. 8.

FIGS. 11a illustrates, in front view the external urinary collection catheter and its applicator which is produced in accordance with the second example shown in FIGS. 8 to 10, before application.

FIG. 11b illustrates, in side view, the external urinary collection catheter and its applicator which is produced in accordance with the second example shown in FIGS. 8 to 10, before application.

FIG. 12a illustrates, in front view a first step in the fitting of the external urinary collection catheter, according to FIGS. 11a and 11b, onto the penis of a patient, using the applicator shown in FIGS. 8 to 10.

FIG. 12b illustrates, in side view, a first step in the fitting of the external urinary collection catheter, according to FIGS. 11a and 11b, onto the penis of a patient, using the applicator shown in FIGS. 8 to 10.

FIG. 13a illustrates, in front view a second step in this fitting.

Figure 2:
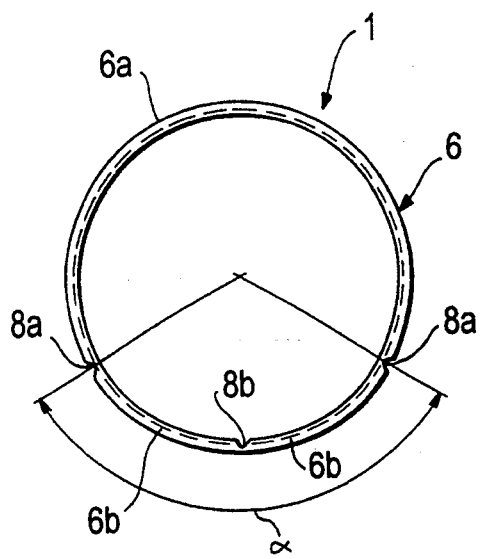
FIG. 2 is a front view of the catheter shown in FIG. 1.
Figure 3:
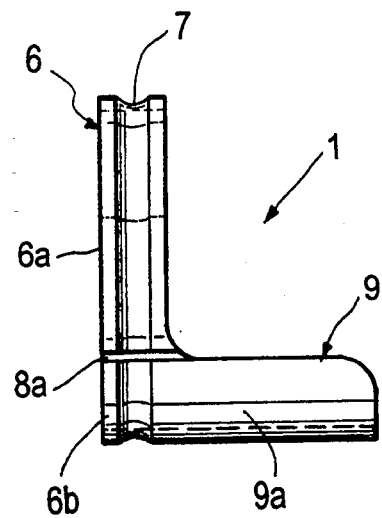
FIG. 3 is a side view of the catheter shown in FIG. 1.
Figure 1:
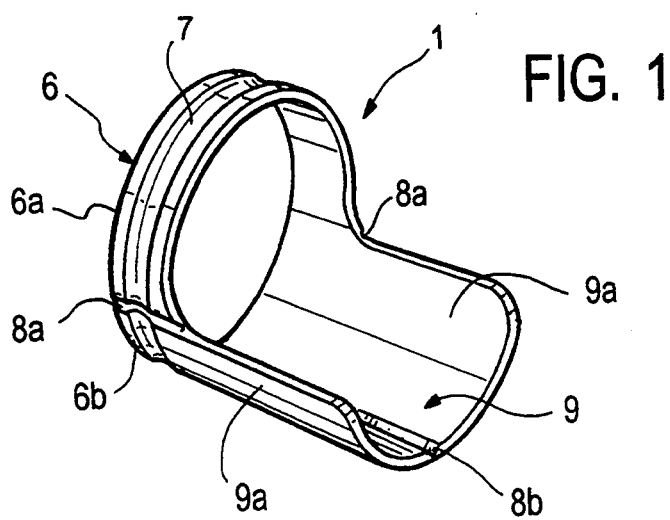
FIG. 1 is a perspective view of a first embodiment of an applicator for an external urinary collection catheter according to the invention.
Figures 4A, 4B:
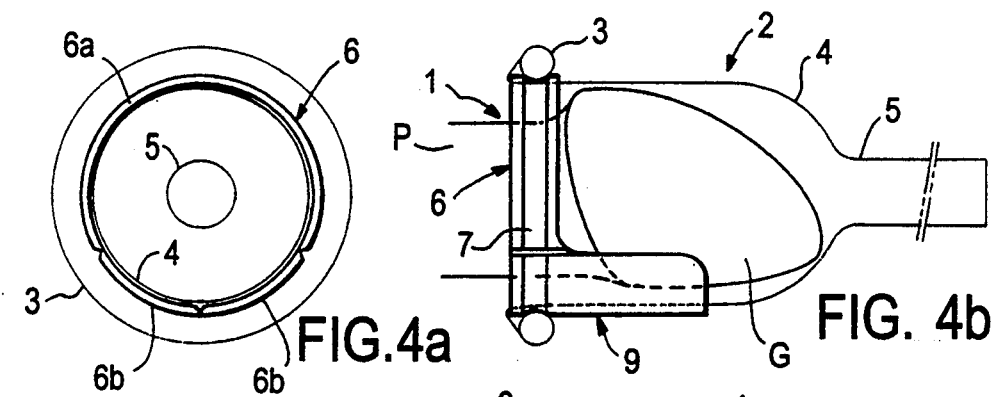
FIG. 4a illustrates, in front view, a first step in the fitting of an external urinary collection catheter onto the penis of a patient, using the applicator shown in FIGS. 1 to 3.
FIG. 4b illustrates, in side view, a first step in the fitting of an external urinary collection catheter onto the penis of a patient, using the applicator shown in FIGS. 1 to 3.

In FIGS. 1 to 3, a first embodiment of an applicator 1 according to the invention has been represented, for an external urinary collection catheter 2 shown in FIGS. 4a, 4b; 5a, 5b; 6 and 7. It comprises, in a conventional manner, a flexible sheath 3, intended to be applied onto the penis of a patient, which is connected to a part 4, for receiving the glans, of cylindrical shape, itself connected to a tube 5 for removing urine (this tube may be connected to urine collection means, not shown).

The applicator 1, for its part, comprises a ring 6 of variable diameter, provided with a peripheral groove 7 for receiving the sheath 3 in the rolled-up position. The ring 6 has a peripheral part 6a, extending over most of the circumference of the ring, and two adjacent peripheral segments 6b, each delimited by folding lines of lesser thickness 8a (joining them to the peripheral part 6a) and 8b (joining them to each other). In this embodiment, the two segments 6b extend, over an angle α of 120° symmetrically with respect to their common folding line 8b. Moreover, the two segments 6b are formed in a single piece with a trough-shaped gripping part 9, extending transversely to the ring 6 (that is to say, substantially coaxially with the part 4 for receiving the glans) in the extension of the segments 6b, and itself separated into two portions 9a by the extension of the folding line 8b common to the segments 6b.

Figures 5A, 5B:
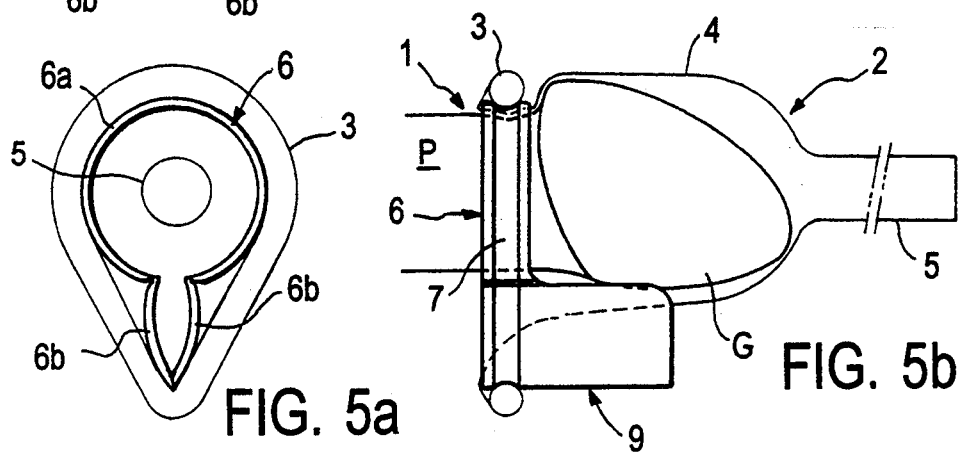
FIG. 5a illustrates, in front view, a second step in this fitting.
Figure 6:
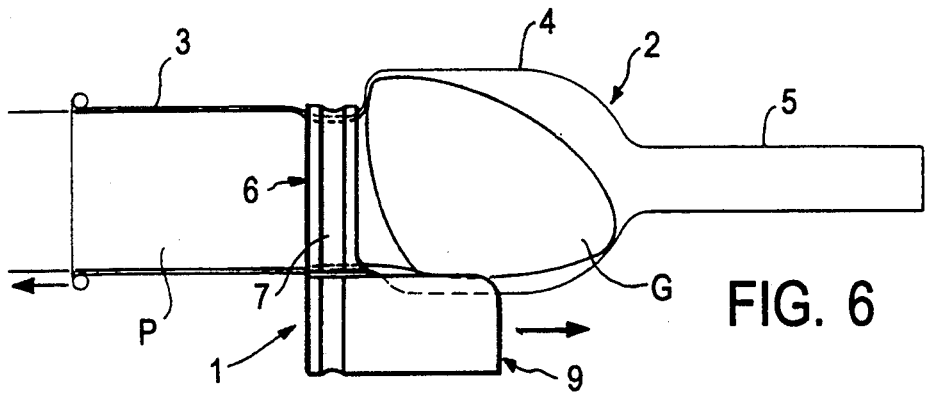
FIG. 6 shows the next-to-last step of this fitting.
Figure 7:
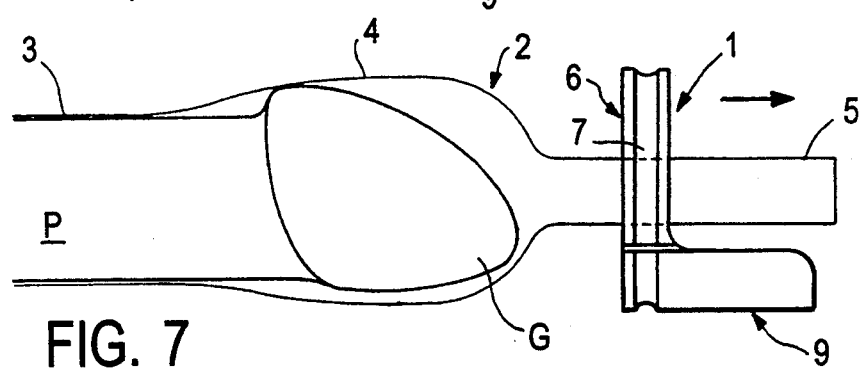
FIG. 7 shows the last step of this fitting.

FIGS. 4a, 4b; 5a, 5b; 6 and 7 show the fitting of the external urinary collection catheter 2 onto the penis P of a patient, with the aid of the applicator 1 shown in FIGS. 1 to 3. With the applicator 1 in place on the catheter 2, and the sheath 3 of the latter arranged, in the rolled state, in the groove 7 of the ring 6, the applicator/catheter assembly is slipped over the glans G of the penis P (the ring 6 must therefore have an initial diameter slightly greater than that of the glans G), the reception part 4 completely surrounding the glans, and the ring 6 of the applicator being situated beyond the glans (the gripping part 9 of the applicator 1 is then facing the underside of the glans G, while extending over a portion of the reception part 4). This initial step is shown in FIG. 4b. By pressing the two portions 9a of the gripping part 9, that is to say, the segments 6b of the ring 6 as well, towards each other, the latter is reduced to a ring substantially defined by the peripheral part 6a (FIGS. 5a and 5b), such that the ring can be caught behind the glans G, and the operator may thus pull on the vigra of the patient, preventing it from retracting, whilst unrolling the sheath 3 onto the penis P (FIG. 6). When the sheath 3 is completely unwound, the catheter 2 is in place, and the operator, by relaxing the pressure on the gripping part 9, allows the ring to resume its initial diameter spontaneously (FIGS. 4a and 4b), so that the applicator 1 can be withdrawn from the catheter 2 (FIG. 7).

In FIGS. 8 to 10, a second embodiment of an applicator 1 according to the invention has been represented, for an external urinary collection catheter 2 shown in FIGS. 11a, 11b; 12a, 12b, 13a, 13b; 14 and 15, here being of the same type as that previously described, and its elements being denoted by the same numerical references.

Moreover, this embodiment of the applicator 1 comprises most of the elements of the applicator 1 in FIGS. 1 to 3, denoted in FIGS. 8 to 10 by the same numerical references. However, in this case, the trough-shaped gripping part 9, extending transversely to the ring 6, and separated into two portions 9a by a central folding line 9b, is no longer formed in a single piece with the segments 6b (constituting, with the peripheral parts 6a, the ring 6), but is integral, at its ends, with the ring 6, in the vicinity of the folding lines 8a joining the segments 6b to the peripheral part 6a of the ring 6. As is seen in FIGS. 8 to 10, the gripping part 9 then hangs from the ring 6, while "freeing" the segments 6b of the latter.

FIGS. 11a and 11b show the advantage of this configuration. It actually allows, as can be seen, the sheath 3 to be kept rolled up before application in the groove 7 of the ring 6, in an unstretched manner, by pushing the two segments 6b towards the inside of the ring 6, and the sheath 3, once unrolled, to be prevented from forming folds.

Figure 14:
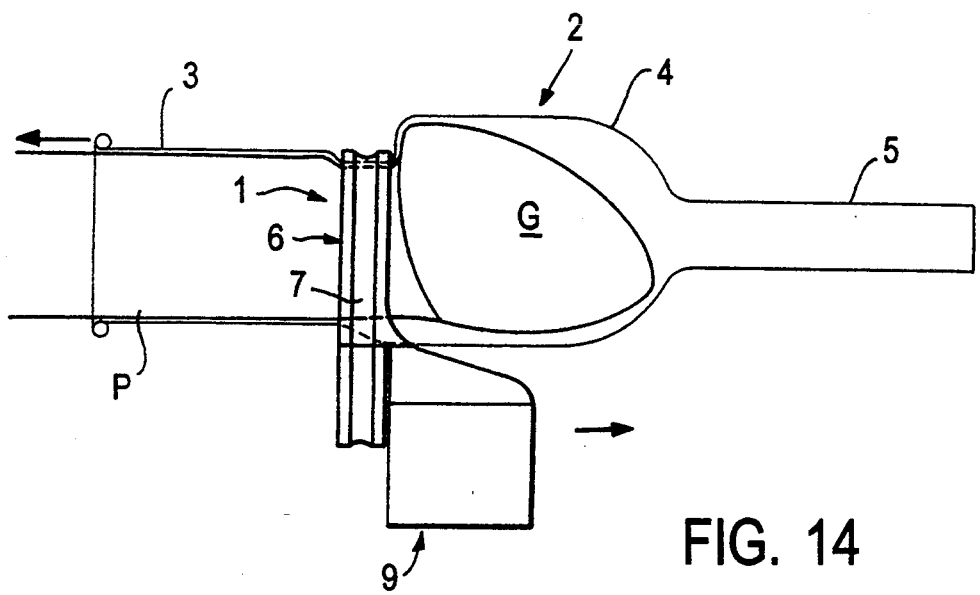
FIG. 14 shows the next-to-last step of this fitting.
Figure 15:
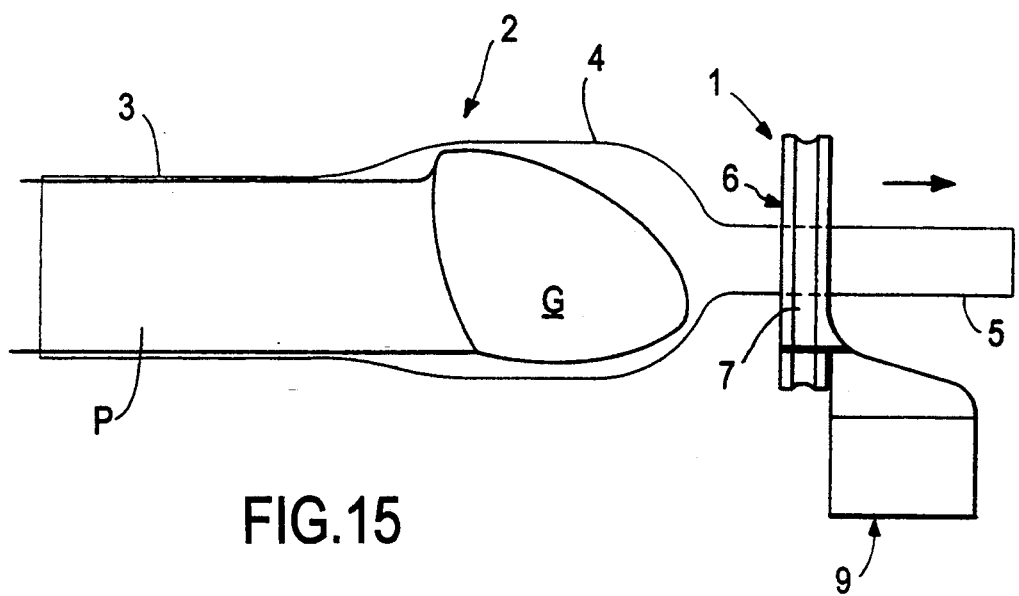
FIG. 15 shows the last step of this fitting.

Moreover, the fitting of the external urinary collection catheter 2 onto the penis P of a patient, with the aid of the applicator 1 shown in FIGS. 8 to 10, is illustrated in FIGS. 12a, 12b; 13a, 13b; 14 and 15. With the applicator 1 in place on the catheter 2, and the sheath 3 of the latter arranged, in the rolled state, in the groove 7 of the ring 6 (the segments 6b then being, obviously, returned into the position where they are in the extension of the peripheral part 6a, stretching the sheath 3, as is seen in FIG. 12a), the applicator/catheter assembly is slipped over the glans G of the penis P, the reception part 4 completely surrounding the glans, and the ring 6 of the applicator being situated beyond the glans (the gripping part 9 of the applicator 1 is then below the glans G, extending over a portion of the reception part 4). This initial step is shown in FIG. 12b. By pressing the two portions 9a of the gripping part 9 towards each other, that is to say, the segments 6b of the ring 6 as well, because of the solid attachment between the gripping part 9 and the segments 6b at the folding lines 8a, the ring is reduced to a ring substantially defined by the peripheral part 6a (FIGS. 13a and 13b), such that the ring can be caught behind the glans G. The operator may thus pull on the virga of the patient, preventing it from retracting, whilst unrolling the sheath 3 onto the penis P (FIG. 14). When the sheath 3 is completely unwound, the catheter 2 is in place, and the operator, by relaxing the pressure on the gripping part 9, allows the ring to resume its initial diameter spontaneously (FIGS. 12a and 12b), so that the applicator 1 can be withdrawn from the catheter 2 (FIG. 15).

I claim:

1. A male urinary collection catheter kit, comprising:
   (a) a catheter (2) having a flexible sheath (3) which is placed in a leaktight manner onto a penis and which is rolled up prior to being placed on the penis, a tubular-shaped part (4) which receives the glans of the penis and which is connected to the sheath (3), and a tube (5) in which urine is removed and which is connected to the sheath (3); and
   (b) an applicator (1) having a resiliently deformable ring (6) the diameter of which may be varied so that it can be slipped over said tubular-shaped part (4), then the diameter can be reduced until the ring (6) is caught behind the glans, then the diameter can be maintained while the virga of the penis is pulled upon to cause it to extend so that the flexible sheath (3) can be unrolled over the penis and then the diameter is capable of spontaneously increasing so that the applicator (1) can be removed from said catheter.

2. The male urinary collection catheter kit as claimed in claim 1, wherein said ring (6) has a peripheral part (6a), which extends over most of the circumference of the ring, and two adjacent peripheral segments (6b), each of which is delimited by folding lines (8a, 8b) of lesser thickness, so that when said two adjacent peripheral segments (6b) are pressed towards each other, the diameter of the ring (6) is reduced until the ring is substantially defined by said peripheral part (6a).

3. The male urinary collection catheter kit as claimed in claim 2, wherein the two adjacent peripheral segments (6b) extend over 120° symmetrically with respect to their common folding line (8b).

4. The male urinary collection catheter kit as claimed in claim 2, further comprising a trough-shaped gripping part (9) which extends transversely to the portion of said ring (6) adjacent to the two segments (6b), the two segments (6b) and the gripping part (9) being formed in a single piece and the gripping part (9) being separated into two portions (9a) by extension of the folding line (8b) common to the two segments (6b).

5. The male urinary collection catheter kit as claimed in claim 2, further comprising a trough-shaped gripping part (9) which extends transversely to said ring (6) and which is separated into two portions (9a) by a central folding line (9b), each of the two portions (9a) having one end which is integral with said ring (6).

6. The male urinary collection catheter kit as claimed in claim 1, wherein said ring (6) has a peripheral groove (7) in it for receiving said sheath (3) while it is still rolled up before it is placed onto the penis.

* * * * *